(12) United States Patent
Brighenti et al.

(10) Patent No.: US 8,939,013 B2
(45) Date of Patent: Jan. 27, 2015

(54) DUCT DETECTOR WITH IMPROVED FUNCTIONAL TEST CAPABILITY

(75) Inventors: Donald D. Brighenti, Westminster, MA (US); Jeffrey R. Brooks, Ashburnham, MA (US)

(73) Assignee: Tyco Fire & Security GmbH, Neuhausen am Rheinfall (CH)

( * ) Notice: Subject to any disclaimer, the term of this patent is extended or adjusted under 35 U.S.C. 154(b) by 270 days.

(21) Appl. No.: 13/422,368

(22) Filed: Mar. 16, 2012

(65) Prior Publication Data

US 2013/0239659 A1    Sep. 19, 2013

(51) Int. Cl.
| G08B 17/10 | (2006.01) |
| G08B 17/103 | (2006.01) |
| G08B 17/107 | (2006.01) |
| G08B 17/12 | (2006.01) |
| G01N 21/53 | (2006.01) |

(52) U.S. Cl.
USPC ........................................................ 73/28.01

(58) Field of Classification Search
USPC ................................. 250/574; 356/239.1, 432
See application file for complete search history.

(56) References Cited

U.S. PATENT DOCUMENTS

| 4,758,827 A * | 7/1988 | Powers ....................... 340/691.7 |
| 5,141,309 A | 8/1992 | Worwag |
| 5,237,264 A * | 8/1993 | Moseley et al. ............... 323/324 |
| 5,400,014 A * | 3/1995 | Behlke et al. .................. 340/630 |
| 5,430,307 A * | 7/1995 | Nagashima ..................... 250/574 |
| 5,523,744 A | 6/1996 | Wieser |
| 5,587,790 A | 12/1996 | Nagashima |
| 6,052,058 A | 4/2000 | Knox |
| 7,012,685 B1 | 3/2006 | Wilson |
| 7,696,891 B2 * | 4/2010 | Whitney ....................... 340/628 |
| 8,305,739 B2 * | 11/2012 | Dozier .......................... 361/627 |
| 2003/0001746 A1 * | 1/2003 | Bernal et al. .................. 340/630 |

FOREIGN PATENT DOCUMENTS

GB        2 415 535 A    12/2005

OTHER PUBLICATIONS

European Patent Office, Extended European Search Report, mailed Oct. 2, 2013, for European Patent Application No. 13158424.5.

* cited by examiner

*Primary Examiner* — Peter Macchiarolo
*Assistant Examiner* — Anthony W Megna Fuentes
(74) *Attorney, Agent, or Firm* — Kacvinsky Daisak Bluni PLLC

(57) ABSTRACT

A device and method for facilitating convenient functional testing of a duct detector is provided. The device includes a duct detector having a remote-controlled test light mounted in a housing thereof, and a detector chamber defined by a filter screen and a plurality of labyrinth members that allow light emitted by the test light to enter the detector chamber. A functional test of the duct detector can be conducted by activating the test light. If the detector is functioning properly, an amount of light emitted by the test light will be detected by the light detector, thereby simulating the presence of an excessive amount of particulate within the detector chamber. The light detector will then generate an output signal that will cause the actuation of alarms and/or the deactivation of a blower system, thereby indicating functionality of the duct detector.

10 Claims, 4 Drawing Sheets

DUCT DETECTOR WITH IMPROVED FUNCTIONAL TEST CAPABILITY

FIELD OF THE DISCLOSURE

The disclosure relates generally to air handling systems, and more particularly to a device and method for facilitating convenient functional testing of a duct detector.

BACKGROUND OF THE DISCLOSURE

Air handling systems, such as heating, ventilation, and air conditioning (HVAC) systems, are an important feature of modern building infrastructure. It is often critical that air which flows though air handling systems be continuously monitored for the presence of impurities that may pose a threat to the health and well-being of a building's occupants. For example, it is common to monitor the levels of oxygen, carbon monoxide, particulate, and smoke in air that flows through a building's air handling system. Such monitoring is typically facilitated by duct detectors that are installed at various locations throughout a building's ductwork.

Unlike conventional smoke detectors and other so-called "point detectors" that are commonly mounted to ceilings or walls to passively sense convection currents of ambient gas, a duct detector is encased in a sealed housing mounted to the exterior of a duct. An inlet conduit is in fluid communication with the interior of the detector housing and extends into the duct to gather air from therein. The gathered air flows into the detector housing, through the duct detector, and back into the duct through an exhaust conduit. The duct detector is thereby able to continuously sample and analyze the large volumes of air that flow through the duct. If certain properties of the sampled air exceed or fall below predetermined limits, the duct detector can be configured to actuate an alarm and/or deactivate blowers that drive air through the air handling system to mitigate the further spread of unsuitable air.

It is known that performance of duct detectors can degrade over time due to reasons such as electrical failure or particulate clogging of a detector's filter screen. Governmental agencies may therefore require that duct detectors be periodically tested to demonstrate proper functionality. Such testing is typically performed by a technician or other individual who manually introduces smoke or particulate into an air handling system, such as from a spray canister, at a location immediately upstream from the duct detector. The smoke or particulate flows into the duct detector and causes the detector to enter an alarm mode if the detector is functioning properly.

A problem commonly associated with testing the functionality of duct detectors in the manner described above is that duct detectors are often installed in elevated locations, sometimes above ceilings, with few surrounding structures capable of supporting the weight of an individual during testing. Detectors that are located in such areas offer poor accessibility, rendering the task of functional testing highly inconvenient and even hazardous. As a result, testing is sometimes not performed as frequently as it should be and, in some cases, is entirely forgone.

SUMMARY

In view of the forgoing, a device and method for facilitating safe and convenient functional testing of a duct detector is disclosed. In particular, a duct detector with improved functional testing capability is disclosed. The duct detector can include many of the components of conventional, commercially available duct detectors as will be appreciated by those of ordinary skill in the art. Particularly, the duct detector can include a main housing, an inlet conduit, an exhaust conduit, a detector assembly, and control circuitry. The detector assembly may include a detector housing, a filter screen, a detector chamber, a light emitter, and a light detector.

In addition to the conventional duct detector components listed above, the duct detector may include a test light disposed within the main housing adjacent to the detector assembly, and a plurality of labyrinth members defining at least a portion of the detector housing, wherein the labyrinth members allow light emitted by the test light to pass through the detector housing.

During typical use of the duct detector, a technician or other individual can activate the test light, such as by transmitting a control signal dictating such action to the control circuitry of the duct detector. If the detector is functioning properly, an amount of light emitted by the test light will pass through the filter screen and labyrinth members of the detector assembly and will be detected by the light detector. The amount of light projected into the detector housing and detected by the light detector should result in a detector output signal that exceeds a predefined trip level if the duct detector is functioning properly.

If the output signal from the light detector exceeds the predefined trip level, the control circuitry will generate an alarm signal indicating that the duct detector is functioning properly. If, upon activation of the test light, the control circuitry does not receive an output signal from the light detector that exceeds the trip level, the control circuitry will not generate the alarm signal and it can therefore be determined that the duct detector is not functioning properly.

A first embodiment of the device disclosed herein can thus include a particulate detector for use in a ventilation duct comprising a main housing and a detector assembly disposed within the main housing. The detector assembly can include a detector housing, a filter screen, a detector chamber, a light emitter, and a light detector. The device can further include at least one test light disposed within the main housing adjacent to the detector assembly, and a plurality of labyrinth members defining at least a portion of the detector housing, wherein the labyrinth members allow light emitted by the at least one test light to pass through the detector housing.

A second embodiment of the device disclosed herein can thus include a particulate detector for use in a ventilation duct comprising a main housing and a detector assembly disposed within the main housing. The detector assembly can include a detector housing, a filter screen, a detector chamber, a light emitter, a light detector, and at least one test light mounted on the detector housing. The device can further include a plurality of labyrinth members defining at least a portion of the detector housing, wherein the labyrinth members allow light emitted by the at least one test light to pass through the detector housing.

A method disclosed herein for testing the functionality of a duct detector can thus include emitting light from at least one test light located in a housing of the duct detector, receiving a portion of the light emitted from the at least one test light at a light detector located in the housing, wherein the received light passes through a plurality of labyrinth members positioned between the test light and the light detector. The method can further include determining if the light received at the light detector exceeds a predetermined threshold and signaling an alarm when the light received at the light detector exceeds the predetermined threshold.

The above-described duct detector and test method thus facilitate convenient functional testing of the duct detector without requiring an individual to access a hard-to-reach, potentially hazardous location or introduce foreign particulate into a duct system.

BRIEF DESCRIPTION OF THE DRAWINGS

By way of example, a specific embodiment of the disclosed device will now be described, with reference to the accompanying drawings, in which.

DETAILED DESCRIPTION

Figure 1:
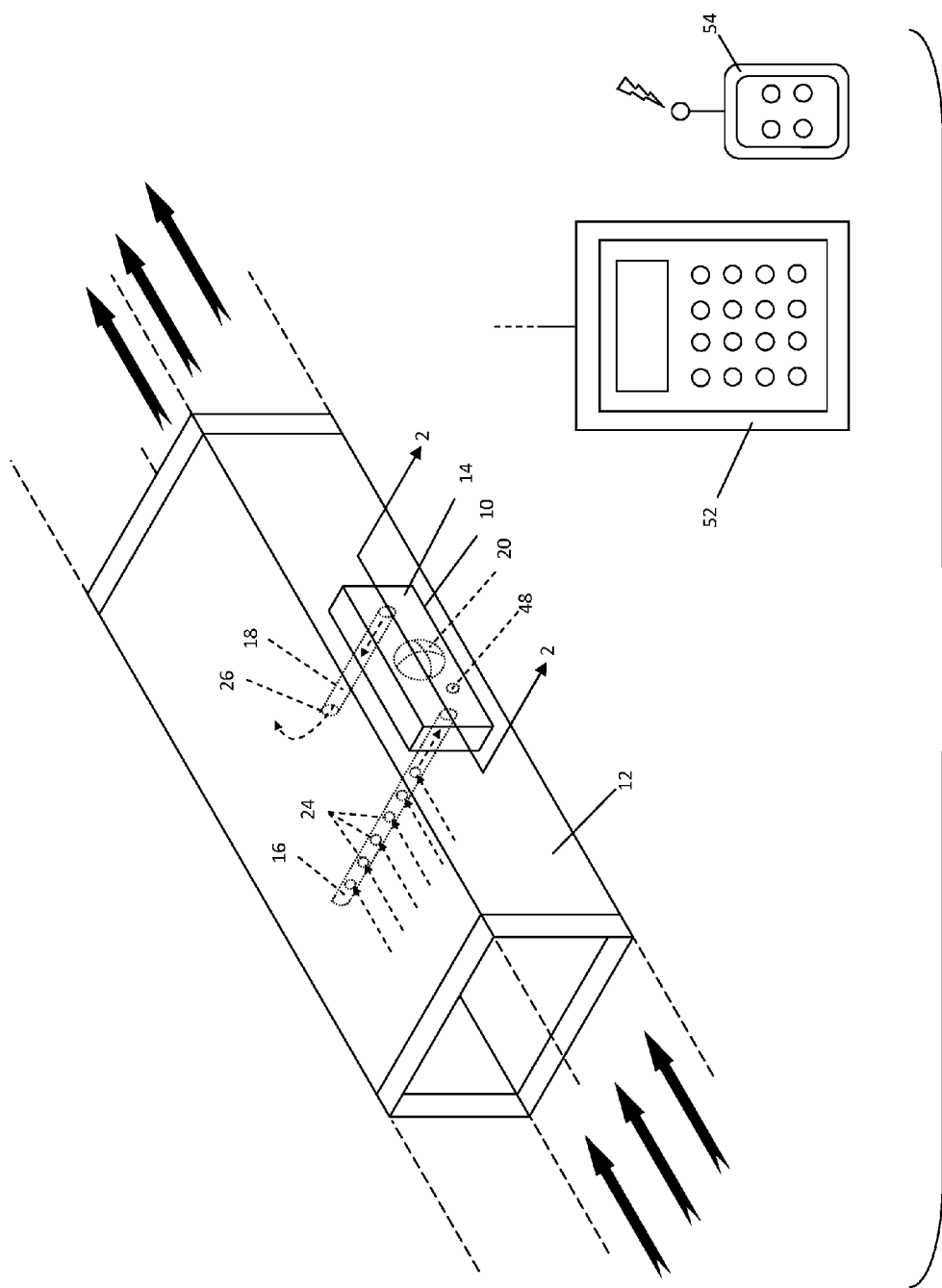
FIG. 1 is a transparent isometric view illustrating the disclosed duct detector installed on a section of duct.

Referring to FIG. 1, an improved duct detector 10 for facilitating convenient functional testing thereof is shown operatively installed on a section of duct 12. It is to be understood that the particular duct 12 is shown by way of example only, and is meant to be representative of any type of duct, such as may be commonly found in a variety of different buildings, and that the duct detector 10 can be employed in the manner described below in numerous other duct configurations. For example, the size and shape of the duct 12 can be varied with little or no effect on the functionality of the duct detector 10.

For the sake of convenience and clarity, terms such as "front," "rear," "top," "bottom," "upstream," "downstream," "inwardly," and "outwardly," will be used herein to describe the relative placement and orientation of the duct detector 10 and its various components, all with respect to the geometry and orientation of the duct detector 10 as it appears in FIG. 1. Particularly, the term "upstream" shall refer to a position nearer the lower left corner of FIG. 1 and the term "downstream" shall refer to a position nearer the upper right corner of FIG. 1. The large arrows shown in FIG. 1 therefore indicate movement in the downstream direction.

Figure 2:
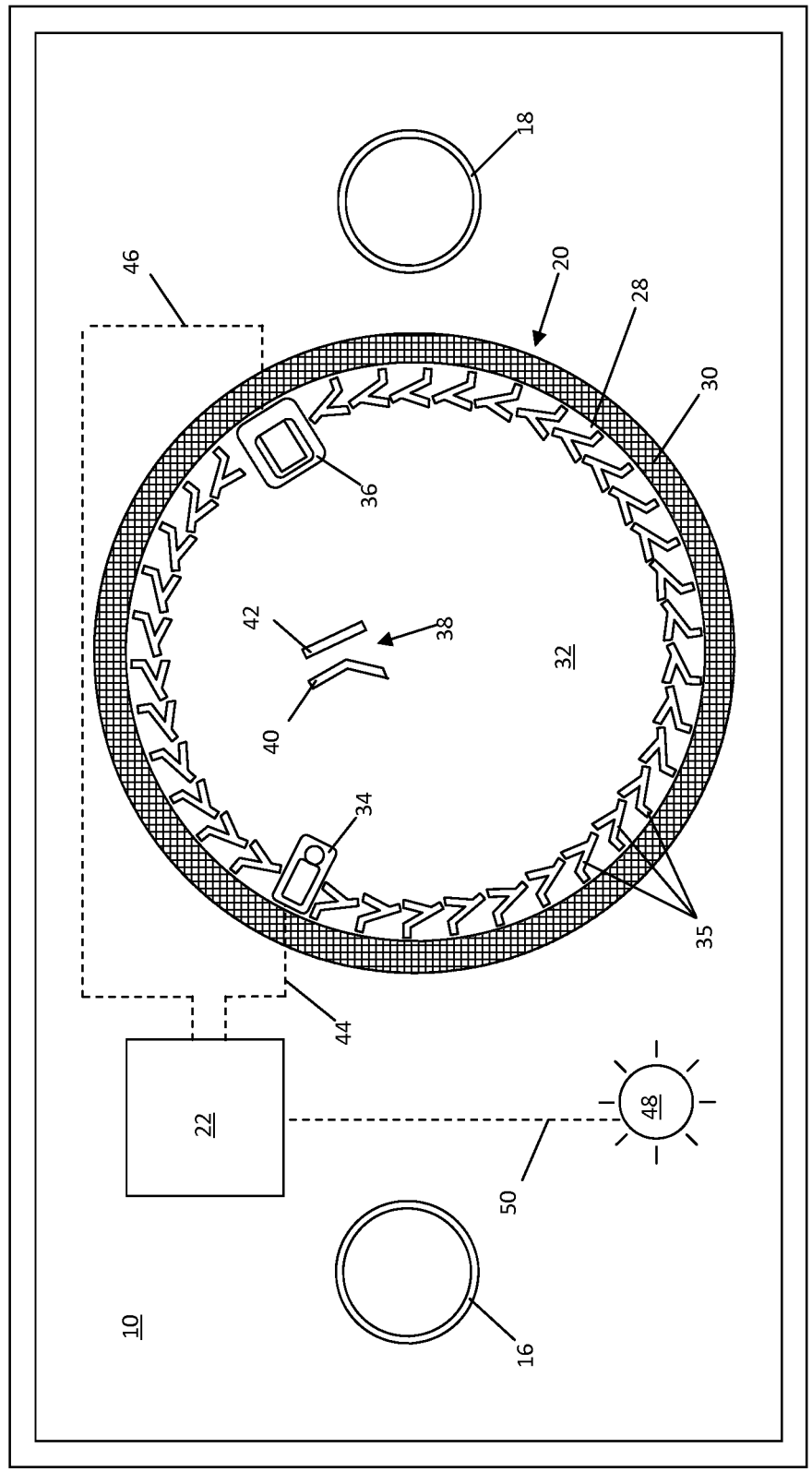
FIG. 2 is a cross-section view of the duct detector of FIG. 1 taken along line 2-2 of FIG. 1.

Referring to FIGS. 1 and 2, the duct detector 10 includes a main housing 14, an inlet conduit 16, an exhaust conduit 18, a detector assembly 20, and control circuitry 22. The main housing 14 may be a hollow body that houses the detector assembly 20 and the control circuitry 22. The inlet conduit 16 may be an elongated, tubular member that extends from an aperture in the rear of the main housing 14 and has a hollow interior that is in fluid communication with the interior of the main housing 14. A series of apertures 24 can be formed in the inlet conduit 16 for allowing air to flow into the inlet conduit 16. The exhaust conduit 18 may be similar to the inlet conduit 16 and may also be an elongated tubular member that extends from an aperture in the rear of the main housing 14 and may have a hollow interior in fluid communication with the interior of the main housing 14. The exhaust conduit 16 may extend from the housing on the opposite lateral side of the detector assembly 20 relative to the inlet conduit 16. An aperture 26 can be formed in the exhaust conduit 18, for example in its distal end, for allowing air to flow out of the conduit 18.

Referring to FIG. 2, the detector assembly 20 of the duct detector 10 may be mounted to the rear wall of the main housing 14, laterally intermediate the inlet conduit 16 and the exhaust conduit 18, and may include a detector housing 28, a filter screen 30, a detector chamber 32, a light emitter 34, a light detector 36, and a septum 38. The detector housing 28 may be a generally dome-shaped member formed substantially of a plurality of angular labyrinth members 35. The labyrinth members 35 define a plurality of tortuous pathways between the interior and exterior of the detector housing 28 and prevent most, but not all, ambient light from entering the detector chamber 32 while simultaneously allowing ambient air to enter and exit the detector chamber 32. It is important to note that, unlike the labyrinth members of conventional detector assemblies which block the entry of substantially all ambient light, the labyrinth members 35 of the detector assembly 20 are configured to allow a small amount of light to enter the detector housing 28 for reasons that will become apparent below. This can be accomplished in a variety of ways, such as by adapting the size, shape, and/or configuration of the labyrinth members 35 to enable a desired degree of light to pass therethrough.

The filter screen 30 of the detector assembly 20 may be formed of metal or plastic and may be located radially outward of, and immediately adjacent to, the labyrinth members 35, thereby surrounding the detector housing 28. The filter screen 30 may serve to prevent large particulate from entering and potentially clogging the labyrinth members 35 and detector chamber 32 while simultaneously allowing ambient air to enter and exit the detector chamber 32. As with the labyrinth members 35 described above, the mesh of the filter screen 30 should not be so dense or occlusive as to block all ambient light from entering the detector chamber 32, for the reasons previously mentioned.

The light emitter 34 and light detector 36 may be mounted within the detector chamber 32, and in one embodiment they are embedded within the detector housing 28, in a substantially opposing relationship (i.e. on opposite lateral sides of the detector chamber 32). In one embodiment the light emitter 34 and light detector 36 may emit and detect infrared (IR) light, respectively. It is contemplated that the emitter 34 and detector 36 can be configured to emit and detect any other type of light, including, but not limited to, visible light and ultraviolet (UV) light.

The septum 38 of the detector assembly 20 can be defined by one or more straight and/or angular walls, such as walls 40 and 42, positioned along a straight line between the emitter 34 and the detector 36. The septum 38 thereby prevents direct light waves projected by the emitter 34 from being received by the detector 36. As previously noted, the interior surfaces of the detector assembly 20 may not reflect light, or may be minimally reflective of light, thereby preventing light projected by the emitter 34 from being reflected to the detector 36 unless reflective foreign matter is present in the detector chamber 32 (as described below).

The control circuitry 22 of the duct detector 10 may be electrically connected to the light emitter 34 and the light detector 36, such as by conductive elements 44 and 46, each of which is representative of one or more power and/or control wires. The control circuitry 22 thereby provides power to, and controls the function of, the emitter 34 and the detector 36 in a predefined manner. For example, the control circuitry 22 may include a microcontroller or processor that periodically flashes the light emitter 34 according to a programmed schedule (e.g. every five seconds). The control circuitry 22 may also monitor output from the light detector 36 and generate an alarm signal if a hazardous condition is detected (described in greater detail below), thereby actuating an audible alarm or deactivating an HVAC blower system, for example. While the control circuitry 22 is shown and described as being an integral, onboard component of the duct detector 10, it is contemplated that some or all of the control circuitry 22 can be located external to the duct detector 10, such as in a fire panel or at another centralized location.

Unlike conventional duct detectors, the duct detector 10 can include a test light 48 mounted within the detector housing 28, adjacent to the detector assembly 20. As will be described in greater detail below, the test light 48 may be used to perform periodic functionality testing of the detector 10. In one embodiment the test light 48 is a light emitting diode (LED), but it is contemplated that any other type of conventional light source can additionally or alternatively be implemented, including, but not limited to, one or more incandescent, halogen, neon, or fluorescent light bulbs. The test light 48 may be configured to emit the same type of light (e.g. IR, visible, ultraviolet, etc.) as the light emitter 34.

Although only one test light 48 is shown in FIGS. 1 and 2, it is contemplated that additional, similar test lights can be mounted within the main housing 14 at various positions around the detector assembly 20. Such additional test lights could be activated simultaneously with the test light 48 to generate a requisite total amount of light for conducting a test (as described below), or could be activated in a cumulative, sequential manner to produce incrementally greater amounts of light, thereby simulating incrementally greater amounts of particulate within the detector chamber 32 (as described below). It is further contemplated that the test light 48 can be mounted on the detector housing 28 and thereby made an integral component of the detector assembly 20.

The test light 48 may be connected to the control circuitry 22, such as by connective element 50, for receiving power and control signals therefrom, but this is not critical. It is contemplated the test light 48 can alternatively receive power and/or control signals from a separate and/or external source via wired or wireless connection. For example, it is contemplated that the test light 48 can receive power from the control circuitry 22, but can receive a manually-actuated control signal through hardwired connection to a remotely-located fire or control panel, such as fire panel 52 in FIG. 1, for activating and deactivating the test light 48. It is further contemplated that the test light 48 can receive power from the control circuitry 22 or the fire panel 52 through hardwired connection, but can receive a wireless control signal from a handheld or fixed-location remote control device, such as remote control device 54 in FIG. 1, such as via radio or infrared signal, or via Wi-Fi or Bluetooth connection. Of course, if such wireless control arrangements are implemented an appropriate wireless receiver may be incorporated into the control circuitry 22 of the duct detector 10.

Referring again to FIG. 1, the duct detector 10 is shown installed on a section of duct 12 in a conventional manner that will be familiar to those of ordinary skill in the art. Particularly, the main housing 14 of the duct detector 10 is mounted to the exterior of the duct 12, such as with mechanical fasteners. The inlet conduit 16 and exhaust conduit 18 extend from the rear of the main housing 14 through corresponding apertures of slightly larger diameter in the duct 12, with the inlet conduit 16 positioned upstream relative to the exhaust conduit 18 and the apertures 24 in the inlet conduit 16 directed upstream. The control circuitry 22 may be connected to a centralized power and control source, such as by a conventional, hardwired connection. For example, the control circuitry 22 can be connected to a centralized fire panel or control panel, such as fire panel 52, from which a building's HVAC system can be controlled. Many other operative configurations are possible but will not be described herein as they are well known in the art.

During typical use, the duct detector 10 functions in substantially the same manner as many other conventional, commercially available duct detectors. Particularly, air from the downstream airflow in the duct 12 enters the inlet conduit 16 through the apertures 24 and is channeled into the main housing 14 (as indicated by the small arrows in FIG. 1). The air then enters and exits the detector chamber 32 through the labyrinth members 35 and the filter screen 30. Finally, the air exits the main housing 14 through the exhaust conduit 18 and is expelled back into the duct through the aperture 26 (as indicated by the small arrows in FIG. 1) where it rejoins the downstream airflow.

As air flows through the detector housing 28 in the manner described above, the control circuitry 22 periodically flashes the light emitter 34, such as at five second intervals, for example. Alternatively, the light emitter 34 can be continuously lit. If the air in the detector chamber 32 does not contain particulate, or does not contain a threshold amount of particulate, little or no light projected by the emitter 34 will be reflected to the detector 36 (for the reasons described above). If, however, the air in the detector chamber 32 contains a threshold amount of particulate, an amount of light will be reflected by the particulate and will be received by the light detector 36. A greater amount of particulate will generally reflect a greater amount of light.

The light detector 36 will then transmit an electrical output signal to the control circuitry 22 that corresponds to the amount of light received by the detector 36. If the electrical signal generated by the light detector 36 exceeds a predetermined "trip level," the control circuitry 22 will determine, such as through the execution of a software program by a processor or hardwired or programmable circuitry in the control circuitry 22, that the particulate content in the airflow has reached an unacceptable level. The control circuitry 22 will then generate an output signal that will actuate an alarm and/or cause a blower system to be deactivated, for example. The occupants of a building are thereby notified of the alarm condition and the further spread of unsuitable air can be mitigated.

It is possible, however, that over time the duct detector 10 will cease to function properly and will therefore fail to generate an alarm signal even when there is an excessive amount of particulate in the airflow through the duct 12. Such failure may be caused by bad electrical connections within the duct detector 10, or by the gradual accumulation of particulate on the filter screen 30. Such accumulation can result in the filter screen 30 becoming clogged, thereby blocking the entry of particulate into the detector chamber 32 that would normally result in an alarm condition. It is therefore desirable to periodically test the functionality of the duct detector 10 to ensure that it is capable of generating an alarm signal under appropriate circumstances.

Figure 3:
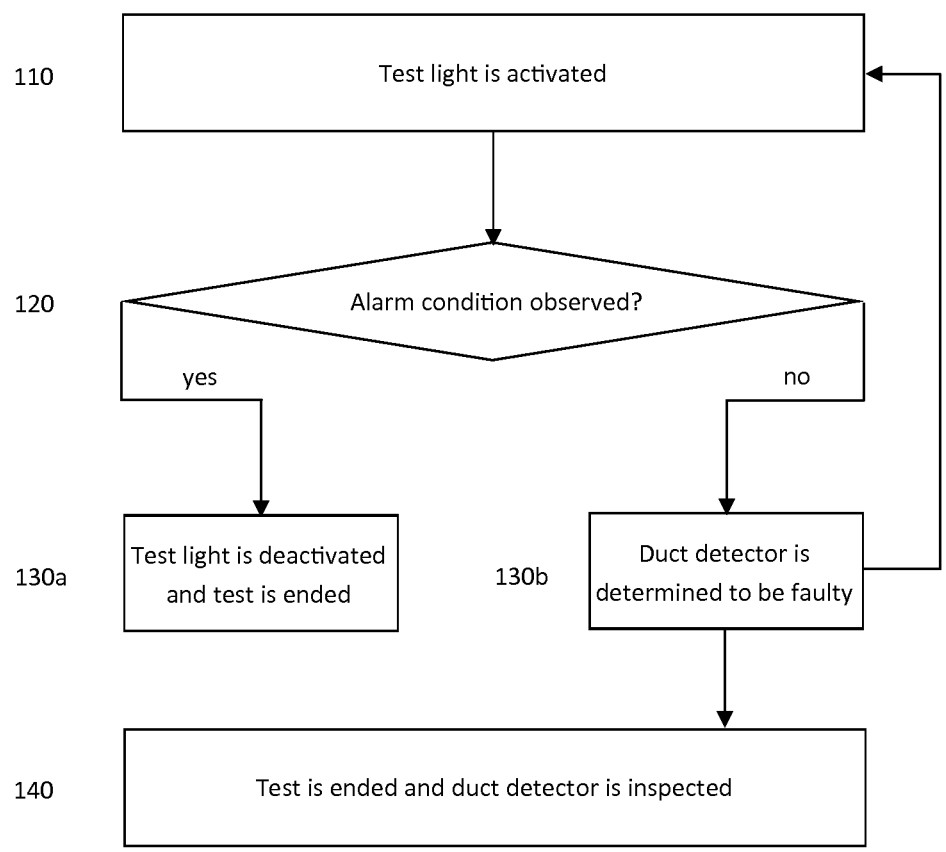
FIG. 3 is a process flow diagram illustrating an exemplary method of testing the functionality of the duct detector of FIG. 1.

Referring to FIG. 3, a method for executing the functional test capability of the duct detector 10 will now be described. Initially, at step 110, a technician or other individual may initiate a functional test of the duct detector 10 by activating the test light 48, such as by transmitting a control signal dictating such action to the control circuitry 22 of the duct detector 10 through a wired or wireless control arrangement as described above. If the duct detector 10 is functioning properly, a sufficient amount of light from the test light 48 will pass through the apertures in the filter screen 30 and through the tortuous channels defined by the labyrinth members 35 and will be detected by the light detector 36. An electrical signal corresponding to the amount of light detected can then be generated by the detector 36 and transmitted to the control circuitry 22 in the manner described above.

At step 120, if the control circuitry 22 receives an output signal from the light detector 36 that exceeds a predetermined trip level, the control circuitry 22 will generate and transmit the above-described alarm signal. For example, the normal operating output voltage of the light detector may be 0.5V; the alarm threshold voltage may be 3V; and the output voltage produced by detection of the test light may be 3.5V. It will be appreciated by those of ordinary skill in the art that these levels may vary greatly depending upon factors such as the particular physical parameters of the detector assembly 20, the type of light emitted by the light emitter 34 and the test light 48, the sensitivity of the light detector 36, etc.

Upon transmission, the alarm signal may actuate corresponding alarms and/or deactivate corresponding blowers of an HVAC system as may normally occur if excessive particulate were detected in the detector chamber 32. Alternatively, the HVAC system could be put into a "test mode" prior to conducting the test and, upon activation of the test light 48 and generation of the alarm signal, an indication could be provided that allows an operator to determine whether the detector passed or failed the test without actuating alarms and/or deactivating blowers of the HVAC system. For example, such an indication could be a light illuminated at a fire panel or a message displayed on an LCD screen of the panel.

At step 130a, the technician can, upon observing the actuation of alarms, deactivation of blowers, and/or other indicia of an alarm condition, determine that the duct detector 10 is functioning properly and can end the functional test, such as by deactivating the test light and reinstating normal operation of the duct detector 10.

If, at step 120, the control circuitry 22 does not receive an output signal from the light detector 36 that exceeds the predetermined trip level, the control circuitry 22 will not generate the above-described alarm signal and the corresponding alarms and blowers will not be actuated and deactivated, respectively. Thus, at step 130b, the technician can, upon observing that the appropriate alarms and blowers have not been actuated and deactivated, determine that the duct detector 10 is not functioning properly. The technician can then re-administer the functional test to confirm the malfunction or, at step 140, can end the test and inspect the duct detector 10 for problems (e.g. a clogged filter screen 30, faulty wiring, etc.).

Figure 4:
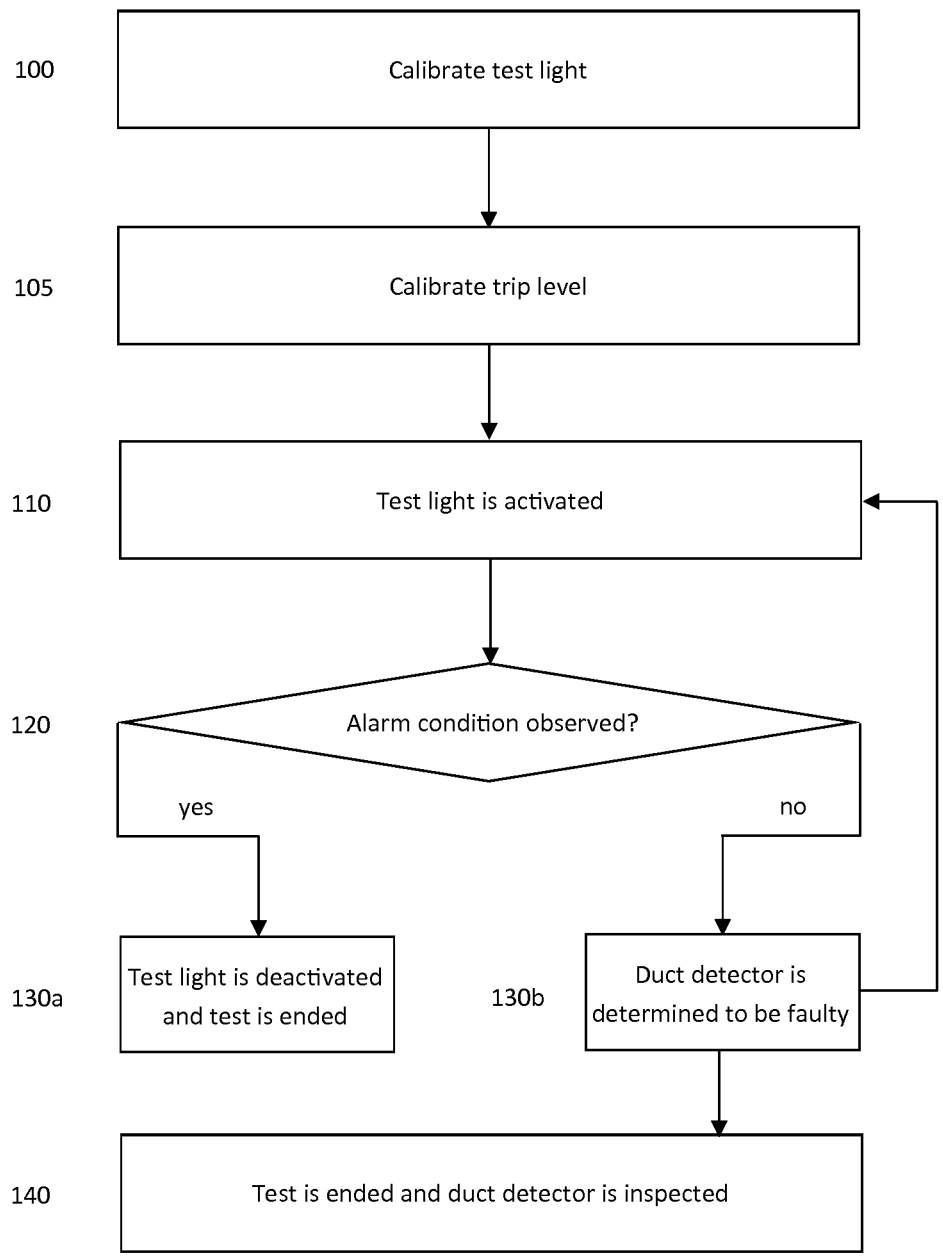
FIG. 4 is a process flow diagram illustrating an alternative method of testing the functionality of the duct detector of FIG. 1.

Of course, in order for the above-described method to be effective for testing the functionality of a duct detector 10, the test light 48 must be able to emit a sufficient amount of light to cause the light detector 36 to generate an output signal that exceeds the predefined trip level when the duct detector 10 is functioning properly. Conversely, the light emitted by the test light 48 must not be so strong that it results in an output signal that exceeds the trip level if the filter screen 30 has become dirty enough to significantly diminish the normal operation of the duct detector 10. The power of the test light 48 should therefore be appropriately calibrated, such as prior to installation of the duct detector 10. Referring to FIG. 4, this step of calibrating the test light 48 can be added to the above-described testing method (shown in FIG. 3), such as at step 100.

A further consideration in calibrating the duct detector 10 is that, due to the modified configuration of the labyrinth members 35 of the duct detector 10 relative to the labyrinth members of conventional duct detectors (described above), a certain, nominal amount of ambient light may be able enter the detector chamber 32 during normal operation. The light detector 36 of the detector assembly 20 may detect this light and send a corresponding output signal to the control circuitry 22. The output signal trip level should therefore be set sufficiently high so that an output signal corresponding to a nominal amount of light received by the light detector 36 will not cause an alarm condition, but should also be set sufficiently low so that an output signal corresponding to an excessive amount of particulate in the airflow will cause an alarm condition. Referring to FIG. 4, this step of calibrating the trip level can be added to the above-described testing method (shown in FIG. 3), such as at step 105.

As used herein, an element or step recited in the singular and proceeded with the word "a" or "an" should be understood as not excluding plural elements or steps, unless such exclusion is explicitly recited. Furthermore, references to "one embodiment" of the present invention are not intended to be interpreted as excluding the existence of additional embodiments that also incorporate the recited features. The terms "control circuit" and "processor" as used herein may refer to circuits and or components that include microprocessors, microcontrollers, microcomputers, programmable logic controllers, application specific integrated circuits, and other programmable circuits, and these terms are used interchangeably herein.

While certain embodiments of the disclosure have been described herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

The invention claimed is:

1. A method for testing the functionality of a duct detector comprising:
   activating a test light located in a main housing of the duct detector using a control device that is remote from the main housing, wherein the main housing is attached to a ventilation duct;
   at a light detector located in a detector housing within the main housing, receiving a portion of light emitted from the test light, wherein the received light passes through a plurality of labyrinth members positioned between the test light and the light detector;
   determining if the light received at the light detector exceeds a predetermined threshold; and
   signaling an alarm when the light received at the light detector exceeds the predetermined threshold.

2. The method of claim 1, wherein determining if the light received at the light detector exceeds a predetermined threshold comprises receiving an output signal from the light detector and comparing the output signal to a predetermined threshold signal level.

3. The method of claim 2, wherein the output signal comprises a current or a voltage.

4. The method of claim 2, further comprising deactivating a blower associated with the duct when the output signal exceeds the predetermined threshold signal level.

5. The method of claim 2, further comprising signaling a clean condition when the output signal exceeds the predetermined signal threshold.

6. A method for testing the functionality of a duct detector comprising:
   activating a test light located in a main housing of the duct detector;
   at a light detector located in the housing, receiving a portion of light emitted from the test light, wherein the received light passes through a plurality of labyrinth members positioned between the test light and the light detector;

receiving an output signal from the light detector and comparing the output signal to a predetermined threshold signal level;

signaling an alarm when the light received at the light detector exceeds the predetermined threshold; and calibrating the test light to emit a predetermined amount of light, wherein the predetermined amount of light is sufficient to generate an output signal that exceeds the predetermined threshold signal level when a filter screen of the duct detector is in a clean condition.

7. The method of claim 6, wherein the predetermined amount of light is not sufficient to generate an output signal that exceeds the predetermined threshold signal level when the filter screen is in a clogged condition.

8. The method of claim 7, wherein the clean condition of the filter is associated with a proper functioning condition of the duct detector, and wherein the clogged condition of the filter is associated with an improper functioning condition of the duct detector.

9. The method of claim 1, wherein emitting light from a test light is controlled by a user via wireless control.

10. The method of claim 1, wherein emitting light from a test light is controlled by a user at a fire panel.

* * * * *